(12) United States Patent
Einig et al.

(10) Patent No.: US 6,726,929 B1
(45) Date of Patent: *Apr. 27, 2004

(54) PHARMACEUTICAL MIXTURE COMPRISING A PROFEN

(75) Inventors: Heinz Einig, Neustadt (DE); Harald Hach, Birkweiler (DE); Richard C. Thompson, Shreveport, LA (US); Raymond Eason, Shreveport, LA (US); Bernd W. Müller, Flintbek (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/868,092

(22) PCT Filed: Dec. 14, 1999

(86) PCT No.: PCT/EP99/09904

§ 371 (c)(1),
(2), (4) Date: Jun. 14, 2001

(87) PCT Pub. No.: WO00/37054

PCT Pub. Date: Jun. 29, 2000

Related U.S. Application Data

(60) Provisional application No. 60/112,954, filed on Dec. 18, 1998.

(51) Int. Cl.[7] ............... A61K 9/14; A61K 9/20; A61K 31/19; A01N 37/10

(52) U.S. Cl. ............ 424/464; 424/465; 424/489; 514/570

(58) Field of Search ............... 424/464, 465, 424/489; 514/570

(56) References Cited

U.S. PATENT DOCUMENTS 6,251,945 B1 * 6/2001 Einig et al. ............... 514/570

FOREIGN PATENT DOCUMENTS

| EP | 131 485 | 1/1985 |
| EP | 298 666 | 1/1989 |
| WO | 93/04676 | 3/1993 |
| WO | 98/58640 | 12/1998 |

* cited by examiner

*Primary Examiner*—James M. Spear
(74) *Attorney, Agent, or Firm*—Keil & Weinkauf

(57) ABSTRACT

A pharmaceutical mixture comprising a profen is described which has a profen content of over 85% and contains up to 1% of a nonionic surfactant having an HLB of $\geq 9$ and also a customary disintegrant and a lubricant and optionally a microcrystalline cellulose.

9 Claims, No Drawings

PHARMACEUTICAL MIXTURE COMPRISING A PROFEN

This application is a 371 of PCT/EP99/09904 filed Dec. 14, 1999 and claims the benefit of Provisional Application No. 60/112,954 filed Dec. 18, 1998.

The present invention relates to a novel pharmaceutical mixture comprising a profen.

In the development of pharmaceutical forms, in particular in the case of profens, the object is generally to find an optimum between 3 opposing objectives:

1. Both from the point of view of the pharmaceutical manufacturer and of the patient, it should be possible to prepare a pharmaceutical form as economically as possible. In the case of tablets, this means that with a fixed dose of active compound which is prespecified out of therapeutic necessity, the amount of the other auxiliaries which are added to the tablets should be kept as low as possible. The lower the amount of auxiliaries, the lower the production costs, which can likewise have an effect on the sale price. The production of tablets should also be as simple as possible and only comprise a few working steps in order likewise to be able to save costs in this way.
2. A tablet should optimally make available the active compound contained therein to the patient. This means an instant-release tablet should disintegrate very rapidly in the digestive fluids and rapidly release the active compound.
3. In order that it is easy to take, the tablet should have as small a form as possible (this applies particularly to high-dose active compounds). Small pharmaceutical forms are better accepted by patients and markedly increase so-called patient compliance.

It is almost impossible to fulfil these 3 requirements at the same time. When processing active compounds which are not extremely highly soluble, rapid release of an active compound from a tablet is achieved only by the addition of relatively large amounts of solubilizing auxiliaries and relatively large amounts of substances which bring about rapid disintegration and thus also rapid dissolution of the tablets. If the active compound can moreover only be tableted with difficulty, the production of a tablet is only possible using additional auxiliaries which compensate the disadvantages of the poor tabletability. Moreover, in the production of ready-to-press tableting materials, in very many cases a laborious granulation step is also necessary beforehand. It is therefore usually impossible to develop a small and economical form.

All these disadvantages are present in the case of the profens. Thus the active compound ibuprofen, for example, is administered in high doses. The dose which is usually not subject to prescription is 200 mg, and in some countries recently 400 mg. For treatment of rheumatic disorders, even pharmaceutical forms having a dose of 600 mg or 800 mg are approved by the pharmaceutical authorities in very many countries.

A further disadvantageous aspect of the profens is that they do not dissolve well. Problems can therefore occur with respect to bioavailability. Therefore for ibuprofen US Pharmacopeia USP XXIII, for example, requires a dissolution rate of at least 80% of the active compound after 60 minutes. In order to achieve a rapid dissolution rate, large amounts of the auxiliaries described above must be added to the ibuprofen in order thus to attain the required high extent of release.

Ibuprofen further shows very poor tableting behavior. The added auxiliaries must therefore at the same time also compensate for this disadvantage. A check of most ibuprofen tablets available on the market shows that the amount of active compound in the total weight of the tablets as a rule is only 55–65%.

It is further common to all these tablets that, for the preparation of the pressable tableting material, a conventional granulation or compaction must be added, since otherwise adequate solidity cannot be achieved during tableting. Granulation, however, is expensive and time-consuming.

A further criterion of the quality of profen-containing tablets is the release of the active compound in vitro. Thus according to Sucker, Fuchs and Speiser in: Pharmazeutische Technologie [Pharmaceutical Technology], Georg Thieme Verlag Stuttgart, 1978, page 283, the dissolution rate of poorly soluble substances can be increased in many cases by the addition of solubilizers. However, if it is attempted to increase the dissolution rate, for example, of ibuprofen by the addition of a solubilizer of the polyethylene glycol type, only minor success is achieved. The same applies if the stabilizer is replaced by a surfactant such as sodium dodecylsulfate.

No tablets are known on the market which contain a high amount of ibuprofen. Although a few ibuprofen-containing tablets having a high active compound content are already known from the literature, these, however, are not available on the market. Thus in EP 0 607 467 A1 pellets are described which have an active compound content of over 90% and which release the active compound (measured according to USP XXII) after 50 minutes only to 15–28%.

In EP 0 456 720 B1 granules are described which have an ibuprofen content of over 90%. The granules were prepared using PVP. Formulations containing PVP, however, exhibit considerable stability problems. Thus the release of active compound from PVP-containing granules is only 20–30% of the original value even 3 months after preparation.

In WO/8902266, a process is described in which, with the aid of an aqueous granulating process in a fluidized bed granulator, granules are prepared which can be pressed directly to give tablets without further additives, but which can only contain up to 85% of ibuprofen. The process is involved and, like all fluidized bed granulating processes, laborious and expensive. Moreover, PVP is employed for binding the granules, which leads to stability problems as mentioned above.

A. Sakr et al. [Pharm. Ind. 60, No. 3 (1998) 257–262] describe an ibuprofen tablet which contains 95% ibuprofen and was prepared by roller compaction. This process, particularly when it is carried out on the plant scale, is very laborious and poorly reproducible. Moreover, these tablets again contain the incompatible PVP. These tablets also do not meet the requirement for a rapid onset of action, as is desired in the case of a painkiller.

Moreover, it is common to all these tablets that, for the preparation of the pressable tableting material, a conventional moist granulation or compaction must again be added as already mentioned above or that PVP must be employed, which admittedly has good binding ability, but does not guarantee stability.

Surprisingly, it has now been found that a specific mixture having a high profen content can be processed very simply to give tablets which meet the highest pharmaceutical demands. In the case of an analgesic this means: small and easy-to-swallow tablets, very rapid onset of action and rapid elimination of the pain. Both are very highly desirable from the point of view of the patient.

The invention relates to a profen-containing pharmaceutical mixture, which has a profen content of over 85%, preferably over 90%, and contains up to 1% of a nonionic surfactant having an HLB of ≧9 and a customary disintegrant and also a lubricant and, if appropriate, celluloses and/or hydroxyalkylcelluloses.

HLB is understood as meaning the "hydrophilic-lipophilic balance", cf. Sucker, Fuchs and Speiser in: Pharmazeutische Technologie [Pharmaceutical Technology], Georg Thieme Verlag Stuttgart, 1978, page 305. The HLB in the mixture according to the invention is ≧9, preferably ≧11 and in particular ≧12.

The details in percent (%) relate to percentage by weight everywhere in the application.

The designation "profen" means antiinflammatory substances containing the structural element

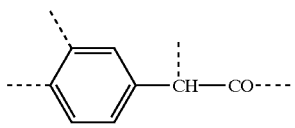

wherein the dotted lines are free bonds.

Examples of such compounds are preferably ibuprofen and its optically active S form. Further suitable profens are flunoxa-profen, flurbiprofen, ibufenac, ibuproxam, ketoprofen and loxo-rofen. The compounds can optionally be present in the form of their physiologically tolerable salts. These are to be understood as meaning the alkali metal and alkaline earth metal salts and also salts with amino acids such as lysine. Preferred are the sodium salts and the salts with lysine.

The term "pharmaceutical mixture" particularly includes administration forms such as tablets, film-coated tablets, sugar-coated tablets and also the mixtures and pellets which are filled into the hard gelatin capsules.

The high active compound content of profen in the administration form is achieved by incorporating into the administration form an amount of up to 1%, preferably 0.01–0.8%, (based on the amount of profen in the administration form) of a nonionic surfactant. Larger amounts of surfactant do not produce any further advantages.

Suitable nonionic surfactants having an HLB of 9 and over are, for example, sucrose esters; partial fatty acid esters of polyhydroxyethylenesorbitan, such as polyethylene glycol(20) sorbitan monolaurate, monopalmitate, monostearate and monooleate; poly-ethylene glycol(20) sorbitan tristearate and trioleate (which are available, for example, under the trade name Tween®; polyethylene glycol(4) sorbitan monolaurate and monostearate; polyethylene glycol(5) sorbitan monooleate, polyhydroxyethylene fatty alcohol ethers such as polyoxyethylene cetyl stearyl ether (which are obtainable, for example, under the trade name Cremophor® O; corresponding lauryl ethers (which are obtainable, for example, under the trade names Brij® 30 and Brij® 35); polyhydroxyethylene fatty acid esters (which are obtainable, for example, under the trademarks Myrj® 45, Myrj® 52 and Myrj® 59); ethylene oxide/propylene oxide block copolymers (which are obtainable, for example, under the trade names Pluronic® and Lutrol®; furthermore sugar ethers and sugar esters; phospholipids and their derivatives; and ethoxylated triglycerides such as the derivatives of castor oil (which are available, for example, under the trade names Cremophor® EL, Cremophor® RH, Cremophor® RH 40, Cremophor® RH 60). Among these, Cremophor® RH 40 and Cremophor® 60 are particularly suitable. The surfactants available under the designation Tween® likewise behave very favorably. Very particular mention is to be made of Tween® 80. The use of mixtures of these surfactants is likewise advantageous.

Customary disintegrants are, for example, sodium carboxymethyl starch and sodium carboxymethylcellulose. Coarse-grain celluloses have the same properties.

The amount of disintegrant in the pharmaceutical form is normally in the range from 1 to 4%.

Suitable lubricants are, for example, magnesium stearate and calcium stearate, stearic acid, stearic acid derivatives (which are available, for example, under the trade names Precirol®, talc, Aerosil®, polyethylene glycols (mainly types having a molecular weight of 4000 and higher) and hydrogenated cottonseed and castor oils.

The amount of lubricant in the pharmaceutical form is normally in the range from 0.1 to 0.7%.

The addition of celluloses or hydroxyalkylcelluloses to the pharmaceutical form is not absolutely necessary, but the addition of a small amount of such a substance proves advantageous. The addition of hydroxyalkylcelluloses, in particular of hydroxymethylpropylcellulose 3 cp, hydroxymethylpropylcellulose 6 cp or hydroxypropylcellulose such as, for example, Klucel® EF, is preferred.

The amount of celluloses and hydroxyalkylcelluloses in the pharmaceutical form is normally in the range from 1 to 4%.

Although further pharmaceutical auxiliaries can be added to the pharmaceutical forms, they are not necessary for their production.

The mean particle size of the profen used does not play any great part in the preparation of the administration forms, as a rule it is 10–100 µm, preferably 20–80 µm.

The novel mixture is especially suitable for the production of solid pharmaceutical forms such as granules in hard gelatin capsules or tablets which contain the profen in an amount from 85–98%, preferably 90–98%, of their total weight.

The expression "pharmaceutical form" should distinguish not only the so-called "finished pharmaceutical form", but also tablets without a coating or, in the case of multilayer tablets, the layer containing the profen or the granules containing the profen, which can be shaped to give pellets.

Tablet coatings are not considered in the calculation of the % content of the pharmaceutical form. If the tablets are press-coated or multilayer tablets, the % details for the profen and the auxiliaries thus relate only to the portions or layers of the pharmaceutical form which contain the profen.

For the preparation of, for example, tablets, the surfactants are preferably mixed in dry form with the profen, that is in the case of a liquid surfactant the addition and dispersion of the surfactant is carried out without further addition of a diluent and in the case of a solid surfactant in some cases without prior micronization.

The surfactants, however, can also be dissolved in water or organic solvents and evenly distributed on the profen. However, the moist mixture then still has to be dried. The amount of water or solvent used here is 3–10% (based on the total amount), clearly below the amount of liquid which is needed for granulation (for example 35–40% based on the total amount).

After addition of the customary auxiliaries, the mixture thus obtained can be compressed directly, that is without granulation, to give tablets.

It was extremely surprising that as a result of the addition of the surfactants mentioned, which, for example, in the case of the polyoxyethylene sorbitan esters are usually highly viscous liquids having a honey-like consistency, profens such as ibuprofen can be processed simply to give tablets having very high pharmaceutical demands. It contradicts all previous experiences that as the result of the addition of a surfactant to a poorly tabletable active compound such as ibuprofen a good compressibility can be achieved. The previous experiences assume that compressibility more likely decreases as a result of the addition of surfactants. Moreover, it was completely surprising that the mixtures thus obtained have a flowability which also cannot nearly be achieved by the sole addition of magnesium stearate and Aerosil®.

Moreover, it is very surprising that the novel tablets even have a very high hardness when they are pressed using an only relatively low compression force.

The following Examples illustrate the invention.

All measurements of active compound releases were carried out according to USP XXIII. A paddle apparatus was used and operated at 50 rpm at pH 7.2.

Unless mentioned otherwise, the ibuprofen used was an ibuprofen having a mean particle size distribution of approximately 50 μm (measured using a Malvern particle meter).

Example 1

A. A mixture of 200 g of ibuprofen, 0.5 g of Tween® 80, 1 g of Aerosil® 200 and 1 g of magnesium stearate as well as 8.5 g of sodium carboxymethyl starch were compressed using a press force of 5–6 kN to give tablets weighing 211 mg having a hardness of 80–90 N. The tablets, which had a weight of 211 mg and an active compound content of 200 mg, exhibited a friability of at most 0.3% (400 revolutions in an Roche Friabilator). The tablets disintegrated within 30–60 sec in water at room temperature. The ibuprofen was released to 100% from these tablets within 5 min.

B. Some of the tablets obtained according to A were coated with a film coating of the following composition:

| | |
|---|---|
| Polydextrose | 28% |
| Hydroxymethylpropylcellulose 2910 3 cp | 30% |
| Hydroxymethylpropylcellulose 2910 15 cp | 10% |
| Polyethylene glycol 400 | 6% |
| Titanium dioxide | 18% |
| Iron oxide | 8% |

1 part by weight of this mixture was processed with 4 parts by weight of a mixture of deionized water and ethanol with intensive stirring to give a suspension. The tablets were coated with this suspension in a laboratory coater. The weight of the film coating per tablet was 12 mg.

The active compound was likewise released from these film-coated tablets within 5 min under the abovementioned conditions.

Example 2

Analogously to Example 1, tablets having an active compound content of 400, 600 or 800 mg of ibuprofen, i.e. tablets having a total weight of 422 mg, 633 mg or 844 mg, were prepared. These tablets exhibited completely identical behavior to those obtained according to Example 1: extreme hardnesses at low press pressure, very low friability, disintegration within 1 min and quantitative release of the active compound from the tablets within 5 min.

These tablets were coated with 22, 33 or 44 mg of film coating analogously to Example 1 B. The active compound was released from these tablets within 5 min under the test conditions indicated in Example 1 B.

Example 3

Examples 1 and 2 were repeated, but the process was carried out with an addition of Tween® 60 or Tween® 40 or Tween® 20 instead of Tween® 80. Tablets having analogous properties to those in Example 1 or 2 were obtained.

Example 4

In this example, 3 batches of 200 mg, 400 mg, 600 mg and 800 mg tablets (i.e. a total of 12 batches) were in each case produced on the production scale (batch size: 1,380 kg)) analogously to Example 1 or 2. The composition of the tablets was as follows:

| | |
|---|---|
| Ibuprofen | 91.0% |
| microcristalline cellulose | 3.75% |
| sodium carboxymethyl starch | 4.0% |
| Tween ® 80 | 0.25% |
| Aerosil ® 200 | 0.5% |
| Magnesium stearate | 0.5% |

The 200 tablets had a weight of 219.8 mg, the 400 mg tablets a weight of 439.6 mg, the 600 mg tablets a weight of 659.3 mg and the 800 mg tablets a weight of 879.1 mg.

In each case, half of the tablets thus obtained were coated with the following amounts of coating layer per tablet:

200 mg tablets with a 8 mg or 90 mg film-coating layer 400 mg tablets with an 12 mg or 120 mg film-coating layer 600 mg tablets with a 16 mg or 180 mg film-coating layer 800 mg tablets with a 20 mg or 220 mg film-coating layer The tables thus obtained having the amounts of active compound in mg indicated in column A were investigated for their hardnesses in N (column B), their disintegration times in sec (column C, and the time up to complete release of active compound (dissolution according to USP XXIII to 100%) in min (column D). The following Table shows the results with the noncoated tablets:

| Batch | A | B | C | D |
|---|---|---|---|---|
| 1 | 200 | 80–90 | 30 | 3 |
| 2 | 200 | 85–90 | 30 | 5 |
| 3 | 200 | 85–95 | 25 | 3.5 |
| 4 | 400 | 85–90 | 25 | 3.5 |
| 5 | 400 | 85–95 | 30 | 4 |
| 6 | 400 | 85–90 | 25 | 3.5 |
| 7 | 600 | 120–130 | 35 | 4 |
| 8 | 600 | 130–140 | 25 | 3.5 |
| 9 | 600 | 110–120 | 30 | 4 |
| 10 | 800 | 140–150 | 35 | 3.5 |
| 11 | 800 | 150–170 | 30 | 4 |
| 12 | 800 | 130–150 | 30 | 3.5 |

The time in which the film-coated tablets prepared from the above tablets and having the low coating amount dissolved quantitatively was approximately 1–2 minutes longer than the times obtained with the uncoated tablets. The time in which the film-coated tablets having the extremely high coating content dissolved was approximately 2–3 minutes longer.

The active compound was released within 5 min from the film-coated tablets having the low coating content under the test conditions indicated in Example 1A. The active compound was released after 6 min from the film-coated tablets having the larger coating content. The low coating content was sufficient in order to make the bad taste of the active compound when swallowing the coated tablets unnoticeable.

In the case of all cores, the friability was less than 0.5%.

Example 5

In this Example, in contrast to Example 1, the surfactant was added to an aqueous solution:

20 kg of ibuprofen were dissolved in 1.4 kg of demineralized water with an aqueous solution of 50 g of Tween® 80 and slowly added to a Diosna® wet mixer in stirring and comminution stage 1. Stirring was then carried out for a further minute under stage 2 in each case. The moistened material was dried in a fluidized bed dryer with incoming air at 60° C. In each case, 100 g of Aerosil® 200 and magnesium stearate as well as 850 g of sodium carboxy-methyl starch were admixed to the dry powder, sieved through a sieve of 1 mm mesh size. The mixture was pressed to give tablets having a weight of 211 mg, corresponding to 200 mg of ibuprofen. The hardness of the resulting tablets (at a press force of 4–5 kN) was 70–80 N, the friability was 0.2% and the disintegration was identical with the tablets obtained according to Example 1. The release of the active compound after 5 minutes was 96%.

Example 6

Example 5 was repeated, but with the difference that the tablets each contained 3 mg of hydroxypropylcellulose (Klucel® EF). At a press force of 4–5 kN, the tablets having a weight of 214 mg exhibited a hardness of 90–110 N. The hydroxypropylcellulose thus exerts an additive effect on the hardness, without adversely affecting the disintegration time and the dissolution of the active compound.

Example 7

Example 5 was repeated, but instead of Tween® 80 the process was carried out using an addition of Tween® 60 or Tween® 40. Tablets having virtually the same properties as in Example 1 were obtained.

Example 8

Example 5 was repeated, but instead of Tween® the same amount of Cremophor® RH 40 was employed. The results achieved with these tablets corresponded to those of Example 1.

Example 9

10 kg of flurbiprofen were mixed with 50 g of Polaxomer® 127, and then 100 g of Aerosil® 200, 100 g of magnesium stearate and 950 g of sodium carboxymethyl starch were admixed. Tablets having a dose of 100 mg of active compound and a weight of 111 mg were obtained. At a press force of 5 kN, they had a resulting hardness of 50 N. The disintegration time of the cores was 30 sec, the friability was less than 0.2% and after 4 min 100% of active compound had dissolved according to USP XXIII.

The tablets were coated with 10 mg each of the film coating described above. After 5 min, the active compound had dissolved quantitatively in the dissolution test.

Example 10

684 g of ibuprofen lysinate were mixed with 2 g of Tween® 80 and then 2 g of Aerosil® 200, 2,5 g of magnesium stearate and 19 g of sodium carboxymethyl cellulose were admixed. The mixture was pressed to give tablets having a weight of 355 mg. At a press force of 5 kN they had a resulting hardness of 120 N. The friability was less than 0.5%. The desintegration time of the cores was 45 sec. After 4 min 100% of the active compound was dissolved according to USP XXIII.

These tablets were coated with 15 mg of the film coating analogously to Example 1B. The active compound was released from the tablets within 5 min under the conditions indicated in Example 1B.

Example 11

256 g of sodium ibuprofenate dihydrate were mixed with 1 g of Myrj® and then 1 g of Aerosil® 200, 1 g of magnesium stearate, 10 g of mikrocristalline cellulose, 8 g of sodium carboxymethyl cellulose and 3 g of Klucel® EF were admixed. The mixture was pressed to give tablets having a weight of 280 mg. At a press force of 6 kN they had a resulting hardness of 90–110 N. The friability was 0.6%. The desintegration time of the cores in water was 60 sec. After 4 min 100% of the active compound was dissolved according to USP XXIII.

Comparison Example 1

Tablets were produced analogously to Example 1, but without addition of Tween® 80. The tablets were unusable, since they did not have adequate hardness.

Comparison Example 2

A mixture of 20 kg of ibuprofen and 50 g of Avicel® PH 102 or Avicel® PH 200 (instead of the Tween® employed in Example 5) was granulated with 1.4 kg of demineralized water and dried in a fluidized bed dryer. The material was then forced through a sieve of mesh size 1 mm. 100 g each of Aerosil 200 and magnesium stearate and also 850 g of sodium carboxymethyl starch were admixed. The mixture was then tableted. The tablets of a weight of 211 mg thus obtained could only be pressed to give tablets of a low hardness of 20–30 N at a press force of 15–18 kN. The excessively low hardness made itself noticeable in the high friability of 4–5%. Moreover, individual tablets had broken into pieces. Under the abovementioned conditions, only 10% of the active compound was released in the course of 5 min.

Repetition of this experiment, but with addition of 100 g of sodium laurylsulfate to the aqueous granulation solution, like-wise led only to a release of the active compound of 20% after min and 29% after 10 min. An improvement in the hardness and the friability could not be recorded compared with the experiment without the added sodium laurylsulfate.

Comparison Example 3

Comparison Example 2 was repeated, but instead of ibuprofen having a particle size of 50 ibuprofen having a particle size of 25 was employed. At a press force of 18–19 kN, only a hardness of 30 N could be achieved. The tablets released only approximately 30% of the active compound in 5 min. As a result of the addition of sodium laurylsulfate, the release after 5 min could only be increased to approximately 45%.

This Comparison Example shows that, according to the invention, without the addition of nonionic surfactants smaller particles dissolve out of the tablets more rapidly than larger ones.

Comparison Example 4

The release rate of ibuprofen from the commercial product Dolomin® was measured, which is recognised as a form having a very rapid dissolution and accordingly also a very rapid absorption of the active compound. The product contains the ibuprofen in the form of its lysinate. The measurement of the release rate of the active compound from this tablet was 28% after 5 min, 59% after 10 min and 83% after 15 min.

What is claimed is:

1. A pharmaceutical mixture comprising a profen, which has a profen content of over 85% and contains up to 1% of a nonionic surfactant having an HLB of $\geq 9$ and also a customary disintegrant and a lubricant.

2. A pharmaceutical mixture comprising a profen as claimed in claim 1, wherein the surfactant employed has an HLB of $\geq 11$.

3. A pharmaceutical mixture comprising a profen as claimed in claim 1, wherein the surfactant employed has an HLB of $\geq 12$.

4. The pharmaceutical mixture claimed in claim 1, wherein the mixture is a tablet.

5. A pharmaceutical mixture comprising a profen as claimed in claim 1 having an active compound content of $\geq 9\%$.

6. A pharmaceutical mixture comprising a profen as claimed in claim 1, which has an in vitro release of the active compound of $\geq 80\%$ after 5 minutes.

7. A pharmaceutical mixture comprising a profen as claimed in claimed in claim 1, which has an in vitro release of the active compound of $\geq 90\%$ after 5 minutes.

8. A pharmaceutical mixture comprising a profen as claimed in claim 1, wherein the profen contained is ibuprofen.

9. A pharmaceutical mixture comprising a profen as claimed in claim 1, wherein the profen contained is flurbiprofen.

* * * * *